US006906533B1

(12) United States Patent
Yoshida

(10) Patent No.: US 6,906,533 B1
(45) Date of Patent: Jun. 14, 2005

(54) TV REMOTE CONTROL UNIT WITH BODY FAT MEASUREMENT FUNCTION

(75) Inventor: Shinji Yoshida, Osaka (JP)

(73) Assignee: Funai Elec. Co. Ltd., Osaka (JP)

( * ) Notice: Subject to any disclaimer, the term of this patent is extended or adjusted under 35 U.S.C. 154(b) by 8 days.

(21) Appl. No.: 10/414,681

(22) Filed: Apr. 16, 2003

(30) Foreign Application Priority Data

Apr. 17, 2002 (JP) .................................... 2002-002160 U

(51) Int. Cl.[7] ........................ G01R 27/08; G01R 27/02; A61B 5/05

(52) U.S. Cl. ........................ 324/692; 324/611; 600/547

(58) Field of Search ................................ 324/611, 605, 324/607, 692; 600/547, 546; 340/825.72; 341/176

(56) References Cited

U.S. PATENT DOCUMENTS 5,372,141 A * 12/1994 Gallup et al. ............... 600/547
6,472,888 B2 * 10/2002 Oguma et al. .............. 324/691
6,487,445 B1 * 11/2002 Serita et al. ................ 600/547
6,509,748 B1 * 1/2003 Cheng ........................ 324/696
6,790,178 B1 * 9/2004 Mault et al. ................ 600/300
2003/0088188 A1 * 5/2003 Maeda et al. ............... 600/547
2003/0090389 A1 * 5/2003 Maeda et al. .......... 340/825.72

FOREIGN PATENT DOCUMENTS

JP 61-166676 10/1986
JP 4-19571 1/1992
JP 7-59022 3/1995
JP 8-154911 6/1996
JP 9-119859 5/1997
JP 10-225442 8/1998
JP 11-285477 10/1999
JP 2000-229072 8/2000
JP 2000-333927 12/2000
JP 2000-342644 12/2000
JP 2001-212098 8/2001
JP 2001-212101 8/2001
JP 2001-346784 12/2001

OTHER PUBLICATIONS

Patent Abstracts of Japan Publication No. 2001–212101, published Aug. 7, 2001.
Patent Abstracts of Japan Publication No. 04–019571, published Jan. 23, 1992.
Patent Abstracts of Japan Publication No. 08–154911, published Jun. 18, 1996 (1 page).
Patent Abstracts of Japan Publication No. 2001–212098, published Aug. 7, 2001 (1 page).
Patent Abstracts of Japan No. 2000–229072 published Aug. 22, 2000 (1 page).
Patent Abstracts of Japan No. 10–225442 published Aug. 25, 1998 (1 page).

* cited by examiner

*Primary Examiner*—Anjan Deb
*Assistant Examiner*—Jeff Natalini
(74) *Attorney, Agent, or Firm*—Osha & May L.L.P.

(57) ABSTRACT

When measuring body fat through use of a TV remote control unit, the body of a person to be subjected to body fat measurement is brought into contact with current application electrodes and voltage measurement electrodes, which are subjected to application of a sinusoidal waveform signal and have a connection configuration of substantially two-electrode type. When a match has arisen between varying voltages developing between the voltage measurement electrodes a predetermined number of times, the voltage is taken as a result of measurement of bio-impedance.

6 Claims, 7 Drawing Sheets

60
61
62 TUNER
63 DEMODULATION CIRCUIT SECTION
64 VIDEO DISPLAY CIRCUIT SECTION
65 OSD CIRCUIT SECTION
66 VIDEO DISPLAY SECTION
67 SOUND OUTPUT CIRCUIT SECTION
68 SPEAKER
74 MICROCOMPUTER
75 POWER SUPPLY SECTION
69 REMOTE CONTROL RECEIVING SECTION
70 BODY FAT COMPUTATION SECTION
71 MEMORY
72 DATA STORAGE SECTION
73 GRAPH PREPARATION SECTION
1

1
20
22
RAM
23
ROM
21
CPU
24
SQUARE WAVEFORM GENERATION CIRCUIT
18
I/O PORT
A/D PORT
17
TRANSMISSION SECTION
28
25
WAVEFORM SHAPING CIRCUIT
7a, 7b
CURRENT APPLICATION ELECTRODES
27
BIO-IMPEDANCE
7c, 7d
VOLTAGE MEASUREMENT ELECTRODEDS
29
DC DETECTION CIRCUIT
4
KEY-OPERATION CIRCUIT
5
LIQUID-CRYSTAL DISPLAY SECTION
6
MEASUREMENT SWITCH

FIG. 5A
VOLTAGE
TIME
FIG. 5B
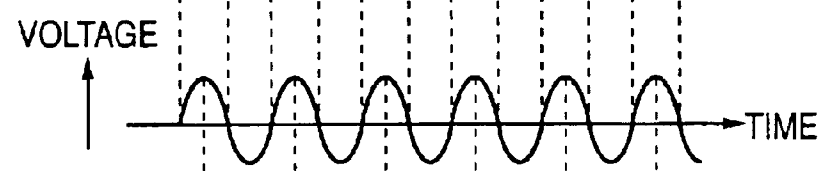
FIG. 5C
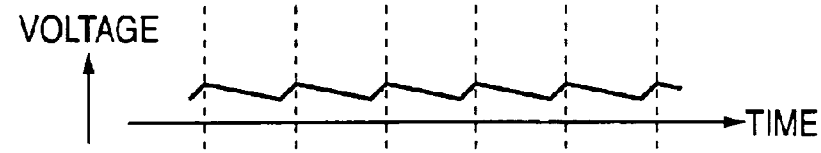
FIG. 5D
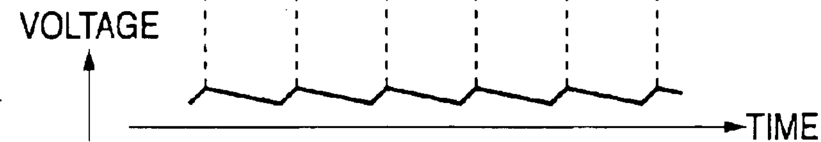

60
61
62
TUNER
63
DEMODULATION CIRCUIT SECTION
64
VIDEO DISPLAY CIRCUIT SECTION
65
OSD CIRCUIT SECTION
66
VIDEO DISPLAY SECTION
67
SOUND OUTPUT CIRCUIT SECTION
68
SPEAKER
75
POWER SUPPLY SECTION
74
MICROCOMPUTER
69
REMOTE CONTROL RECEIVING SECTION
70
BODY FAT COMPUTATION SECTION
71
MEMORY
72
DATA STORAGE SECTION
73
GRAPH PREPARATION SECTION
1

TV REMOTE CONTROL UNIT WITH BODY FAT MEASUREMENT FUNCTION

The present disclosure relates to the subject matter contained in Japanese Utility Model Application No. 2002-002160 filed Apr. 17, 2002, which is incorporated herein by reference in its entirety.

BACKGROUND OF THE INVENTION

1. Field of the Invention

The invention relates to a TV remote control unit having a body fat measurement function which measures percent body fat of a person to be subjected to measurement (hereinafter simply called a "user") through use of a TV remote control by way of which an operation is performed for selecting a TV broadcast channel or a recording channel oil a video recorder.

2. Description of the Related Art

A conventionally-known body fat measurement device requires a user to enter body data, such as the user's weight, height, gender, and age; measures bio-impedance by causing a feeble current to flow through the user's body according to a four-electrode method employing two sets of paired electrodes; and computes the user's body fat (e.g., percentage body fat or the amount of body fat) on the basis of the thus-measured bio-impedance and the body data.

Known body fat measurement devices of this type include a device which performs measurement when the user grips one of each pair of electrodes with his/her left hand and the other of each pair of electrodes with the right hand, and a device which performs measurement when the user places his/her left foot on one of each pair of electrodes and the right foot on the other of each pair of electrodes. Many body fat measurement devices of these types are commercialized as products specifically designed for measuring body fat.

In order to manage health care through cooking through use of a TV remote control unit, a known TV set is described in, e.g., JP-A-7-59,022. The name of a dish and the names of materials for the dish are specified by operation of the TV remote control unit. A microcomputer provided in the TV set computes a calorific value of the dish specified by the TV remote control unit or calorific values of the ingredients specified by the same. The thus-computed calorific value(s) is displayed on the screen of the TV set.

A weight scale having the function of measuring percent body fat as well as the function of measuring a weight has also been known as described in, e.g., JP-A-9-119859. The weight scale measures the user's weight through use of a heated toilet seat. Electrode sections are provided at a plurality of locations for detecting electrical resistance of the user and converting the thus-detected resistance into an electric signal. On the basis of the electric signals output from the electrode sections, an internal resistance value is determined. Percent body fat is computed from the internal resistance value and the weight, and the thus-computed percent body fat is displayed on display means.

Body fat measurement devices as described in, e.g., JP-A-11-285477 and;JP-A-2000-333927, have been known as body fat measurement devices to be used solely for measuring body fat (i.e., percent body fat).

The body fat meter described in the former patent publication comprises impedance measurement means for measuring bio-impedance on the basis of variations in the value of an electric current flowing through electrodes for measuring impedance; computation processing means for computing body data, such as percent body fat and the amount of fat, from the measured bio-impedance and personal data, such as a weight and a height; and data communication means for establishing data communication with external devices, such as a weight scale, a height scale, or a data processor. Particularly, electrodes for bio-impedance measurement are given the function of a data communication connection terminal. Use of a mode changeover switch enables switching between an impedance measurement mode and a data communication mode, thereby obviating connection terminals specifically designed for only data communication.

The percent body fat meter described in the latter patent publication performs the following operations. Namely, a first left backside electrode and a second left backside electrode are brought into contact with the left-side part of the user's backside. Similarly, a first right backside electrode and a second right backside electrode are brought into contact with the right-side part of the backside. A first hand electrode and a second hand electrode are brought into contact with either the right hand or the left hand of the user. Among a total of six electrodes; that is, three pairs of electrodes, each pair consisting of two electrodes brought into contact with the same area of the body, an RF signal is applied to the first electrodes of arbitrary two pairs, and bio-resistance potential is detected from the second electrodes of the same pairs, thereby measuring bio-impedance. Percent body fat, including percent body fat of a body section of the body, can be computed.

A massage chair equipped with a body fat meter has also been known, as described in, e.g., JP-2000-342644. The massage chair comprises body impedance measurement means for measuring body impedance byway of electrodes to be brought into conductive contact with the human body; personal data input means for inputting personal data such as the user's gender, age, height, and weight (body data); and percent body fat computation means for computing percent body fat on the basis of the body impedance and the personal data. The user can measure body fat while seated on the massage chair.

A portable cellular phone and a PHS (personal handy-phone system), which are,equipped with features of an exercise meter and those of a body fat meter, have hitherto been known; for example, a portable cellular phone/PHS (personal handy-phone system) with an exercise meter as described in, e.g., JP-A-2001-346784. The portable cellular phone/PHS having an exercise meter comprises body impedance measurement means for measuring body impedance via electrodes, and percent body fat computation means for computing percent body fat on the basis of the thus-measured body impedance. The thus-computed percent body fat is displayed on the display section of the portable cellular phone.

A remote control unit described in, e.g., JP-UM-A-61-166676, is known as easing stress by use of a TV remote control unit. The remote control unit measures a resistance value obtained by bringing electrodes into contact with the human body, and/or a skin temperature obtained by bringing a temperature sensor into contact with, the human body. Measurement results are displayed on the screen of a TV set or the like. Therefore, the user measures, e.g., a skin temperature through use of the remote control unit and is subjected to suggestion, for example, "your feet and hands are becoming warmer," so as to ease stress while viewing the skin temperature displayed on the, TV screen. Thus, the user can exercise easing of stress by mastering how to increase the skin temperature.

Many related-art body fat measuring devices are commercialized as single commodity products specifically designed for measuring body fat. Electric appliances—which are equipped with the function of measuring body fat and are available within arm's reach in a room at all times—are few in number. In the meantime, there are hybrid products, such as a weight scale and a bath, which are provided with a body fat measurement function. However, these hybrid products are not available at all times within arm's reach in a room. Therefore, these products are unsuitable for measuring body fat when the user feels like measuring body fat. For these reasons, in order to measure body fat whenever the user desires, the user must purchase a body fat measurement device which is available as a single product, thus posing economical burden to the user.

A conceivable measure is to impart a body fat measurement function to a TV remote control unit frequently used in a home. However, according to the above-described related-art techniques, body fat is not measured through use of a TV remote control unit.

The TV set described in JP-A-7-59022 computes a calorific value of the dish specified by the remote control unit or calorific values of ingredients for the dish specified by the same. The TV set does not measure body fat and hence cannot solve the problem.

The weight scale described in JP-A-9-119859 is a hybrid commodity product which measures body fat through use of the heated toilet seat. The weight scale does not measure body fat through use of a TV remote control unit and hence cannot solve the problem.

The body fat meter described in JP-A-11-285477 is a single commodity product aimed at obviating the connection terminal specifically designed for data communication, by providing the bio-impedance measurement electrode to be used for measuring body fat with the function of the data communication connection terminal, and enabling switching between the impedance measurement mode and the data communication mode through use of the mode changeover switch. The body fat meter does not measure body fat through use of a TV remote control unit and hence cannot solve the problem.

The percent body fat meter described in JP-A-2000-333927 is a single commodity product which performs the operations of: bringing the first left backside electrode and the second left backside electrode into contact with the left-side part of the user's backside; bringing the first right backside electrode and the second right backside electrode into contact with the right-side part of the backside; bringing the first hand electrode and the second hand electrode into contact with either the right hand or the left hand of the user; applying an RF signal to the first electrodes of two arbitrary pairs selected from among a total of six electrodes; that is, three pairs of electrodes, each pair consisting of two electrodes to be brought into contact with the same area of the body; detecting bio-resistance potential from the second electrodes of the same pairs, thereby measuring bio-impedance; and computing percent body fat, including percent body fat of the body section of the body. The percent body fat meter does not measure body fat through use of a TV remote control unit and hence cannot solve the problem.

The massage chair described in JP-A-2000-342644 is a hybrid commodity product which comprises the body impedance measurement means for measuring body impedance by way of electrodes to be brought into conductive contact with the human body; the personal data input means for inputting personal data such as the user's gender, age, height, and weight (body data), and the percent body fat computation means for computing percent body fat on the basis of the body impedance and the personal data; and which enables the user to measure body fat while seated on the massage chair. The massage chair does not measure body fat through use of a TV remote control unit and hence cannot solve the problem.

The portable cellular phone/PHS equipped with an exercise meter described in, e.g., JP-2001-346784 is a hybrid commodity product which is formed on the basis of a portable cellular phone; which comprises the body impedance measurement means for measuring body impedance via electrodes, and the percent body fat computation means for computing percent body fat on the basis of the thus-measured body impedance; and which displays the thus-computed percent body fat on the display section of the portable cellular phone. The portable cellular phone/PHS does not measure body fat through use of a TV remote control unit and cannot solve the problem.

The remote control unit described in JP-UM-A-61-166676 is intended for easing stress by mastering how to increase a skin temperature through measurement of a resistance value obtained by bringing electrodes into contact with the human body and/or a skin temperature obtained by bringing a temperature sensor into contact with the human body, and by being subjected to suggestion, e.g., "your legs and hands are becoming warmer," so as to ease stress while viewing the skin temperature displayed on the TV screen.

SUMMARY OF THE INVENTION

The invention has been conceived to solve the problem and aims at providing a TV remote control unit equipped with a body fat measurement function which enables easy measurement of body fat by imparting the function of body fat measurement to a TV remote control unit and which facilitates the structure of the body fat measurement feature by employing bio-impedance measurement electrodes of substantially two-electrode type.

To achieve the object, a first aspect of the invention provides a TV remote control unit comprising: a key operation section having a plurality of keys to be used for performing operations for setting a channel of a TV set and a mode; a transmission section for transmitting, to the TV set, an operation signal corresponding to key operation performed by way of the key operation section; a microcomputer which controls the key operation section and the transmission section and performs predetermined processing; a square wave form generation circuit for generating a square signal of predetermined frequency; a waveform shaping circuit for converting the square signal output from the square waveform generation circuit into a sinusoidal waveform signal; a pair of current application electrodes which constitute a closed circuit upon contact with the body of a person whose body fat is to be measured and causes an electric current stemming from a sinusoidal waveform signal output from the waveform shaping circuit to flow through the body of the person; a pair of voltage measurement electrodes for extracting a potential difference between the current application electrodes developing from the current flowing through the body of the person as a measurement voltage relevant to bio-impedance of the person; a d.c. detection circuit for subjecting the voltage extracted from the voltage measurement electrodes to d.c. detection; and an analog/digital conversion circuit for converting into a digital value a detection voltage having been subjected to d.c. detection by the d.c. detection circuit, wherein a substantial two-electrode type is established by connecting one of the pair of current application electrodes to one of the pair of voltage measurement electrodes and connecting the other electrode of the pair of current application electrodes to the other electrode of the pair of voltage measurement electrodes, wherein the microcomputer comprises: pacemaker checking;means that displays check items to be used for determining whether or not the person has a pacemaker at the time of measurement of body fat of the person; body data setting means which sets body data required for measuring body fat of the person, including the person's weight, age, height, and gender, when the pacemaker check means determined that the person does not to have a pacemaker and when the pacemaker is determined not to exist; and measurement means which, when the body of the person has been brought into contact with at least either the current application electrodes or the voltage measurement electrodes, takes a digital value obtained when a match has consecutively arisen between digital values a predetermined number of times within a predetermined sampling cycle as a result of measurement of bio-impedance required for computing body fat of the person, and wherein the result of measurement of the bio-impedance and the body data are transmitted to the TV set by way of the transmission section; body fat of the person is computed on the basis of the bio-impedance and body data received by the TV set; and the result of computation is displayed on a screen of the TV set.

According to the invention, setting of a channel (setting of a TV broadcast channel or a recording channel of a video recorder) and setting of a mode (setting of a mode for receiving a TV broadcast and recording a video program) can be performed through use of the TV remote control unit. Further, body fat measurement of a person whose body fat is to be measured can also be performed through use of the TV remote control unit. Particularly, the electrodes to be used for measuring bio-impedance of the person adopt a substantially two-electrode type. Hence, the configuration to be used for measuring bio-impedance becomes simple.

At the time of measurement of the person's body fat, check items to be used for determining whether or not the person has a pacemaker are displayed. After the person has effects settings such that he/she does not have any pacemaker and the pacemaker has been determined not to exist, measurement of body fat because feasible, thereby enhancing safety.

After safety has been ascertained, the body data required for measuring body fat of the person, including the person's weight, age, height, and gender, are set in the microcomputer through key-operation of the key-operation section. Subsequently, the body of the person is brought into contact with at least either the current application electrodes or the voltage measurement electrodes. A digital value obtained when a match has consecutively arisen between digital values a predetermined number of times within a predetermined sampling cycle is taken as a result of measurement of bio-impedance required for computing body fat of the person. In this way, when the digital value obtained when a match has consecutively arisen between digital values a predetermined number of times within a predetermined sampling cycle is taken as a result of measurement of bio-impedance, a highly reliable measurement result is obtained.

The result of measurement of the bio-impedance and the body data are transmitted to the TV set by way of the transmission section; body fat of the person is computed on the basis of the bio-impedance and body data received by the TV set; and the result of computation is displayed on a screen of the TV set.

A second aspect of the invention provides a TV remote control unit comprising: a key operation section having a plurality of keys to be used for performing operations for setting a channel of a TV set and a mode; a transmission section for transmitting, to the TV set, an operation signal corresponding to key operation performed by way of the key operation section; a control processing section which controls the key operation section and the transmission section and performs predetermined processing; electric signal generation means for generating an electric signal of predetermined frequency; and a bio-impedance measurement electrode which constitutes a closed circuit upon contact with the body of a person whose body fat is to be measured, causes an electric signal output from the electric signal generation means to flow through the body of the person, and extracts a potential difference developing in the body of the person from the current flowing through the body of the person as a measurement voltage pertaining to bio-impedance of the person, wherein the control processing section comprises: body data setting means which sets body data required for measuring body fat of the person, including the person's weight, age, height, and gender; and measurement means which, when the body of the person has been brought into contact with at least either the current application electrodes or the voltage measurement electrodes, takes a digital value obtained when a match has arisen between digital values a predetermined number of times within a predetermined sampling cycle as a result of measurement of bio-impedance required for computing body fat of the person, and wherein the result of measurement of the bio-impedance and the body data are transmitted to the TV set by way of the transmission section, and the TV set computes body fat of the person from the received bio-impedance and body data and displays the result of computation on a screen of the TV set.

According to the invention, setting of a channel (setting of a TV broadcast channel or a recording channel of a video recorder) and setting of a mode (setting of a mode for receiving a TV broadcast and recording a video program) can be performed through use of the TV remote control unit. Further, body fat measurement of a person whose body fat is to be measured can also be performed through use of the TV remote control unit. Particularly, the electrodes to be used for measuring bio-impedance of the person adopt a substantially two-electrode type. Hence, the configuration to be used for measuring bio-impedance becomes simple.

At the time of measurement of body fat of the person whose body fat is to be measured, body data required for measuring body fat of the person, including the person's weight, age, height, and gender, are set in the control processing section through key-operation of the key-operation section. Subsequently, the body of the person is brought into contact with the bio-impedance measurement electrodes, and when digital values output from the bio-impedance measurement electrode have coincided with each other a predetermined number of times within a predetermined sampling cycle, the voltage is taken as a result of measurement of bio-impedance to be used for computing the person's body fat. Thus, the voltage value obtained when the match has arisen a predetermined number of times is taken as a result of measurement of the bio-impedance. Hence, a highly reliable measurement result is obtained.

The result of:measurement of the bio-impedance and the body data are transmitted to the TV set by way of the transmission section, and the TV set computes body fat of the person from the received bio-impedance and body data and displays the result of computation on a screen of the TV set.

According to a:third aspect of the invention, the TV remote control unit provided with a body fat measurement function according to the second aspect is characterized in that the electric signal generation means has a square wave form generation circuit for generating a square waveform signal of predetermined frequency and a waveform shaping circuit for converting a square signal output from the square waveform generation circuit into a sinusoidal waveform signal, and outputs a sinusoidal waveform signal. A highly accurate sinusoidal waveform signal can be used for measuring the bio-impedance of the user. Further, if the frequency of the square signal is changed, the frequency of the output sinusoidal waveform signal can also be changed. Hence, the accuracy of measurement of impedance is improved, so long as the frequency of the sinusoidal waveform signal has been set to a frequency at which the minimum error arises in an error of measurement of bio-impedance beforehand.

According to a fourth aspect of the invention, the TV remote control unit provided with a body fat measurement function according to the second aspect is characterized in that the bio-impedance measurement electrode has a pair of current application electrodes which constitute a closed circuit upon contact with the body of a person whose body fat is to be measured and causes an electric current stemming from a sinusoidal waveform signal output from the waveform shaping circuit to flow through the body of the person and a pair of voltage measurement electrodes for extracting a potential difference between the current application electrodes developing from the current flowing through the body of the person as a measurement voltage relevant to bio-impedance of the person, and the bio-impedance measurement electrode establishes a substantial two-electrode type by connecting one of the pair of current application electrodes to one of the pair of voltage measurement electrodes and connecting the other electrode of the pair of current application electrodes to the other electrode of the pair of voltage measurement electrodes. Hence, measurement of bio-impedance substantially requires four electrodes, but the number of electrodes is reduced to substantially two electrodes. The configuration of the TV remote control unit is simplified by the amount corresponding to the number of electrodes reduced.

According to a fifth aspect of the invention, the TV remote control unit provided with a body fat measurement function according to the second aspect is characterized in that a d.c. detection circuit subjects the voltage extracted from the voltage measurement electrodes to d.c. detection; an analog/digital conversion circuit converts into a digital value a detection voltage having been subjected to d.c. detection by the d.c. detection circuit; and a digital value obtained when a match has consecutively arisen between digital values a predetermined number of times within a predetermined sampling cycle is taken as a result of measurement of bio-impedance required for computing body fat of the person. Hence, a highly stable result of measurement of bio-impedance is obtained.

According to a sixth aspect of the invention, the TV remote control unit provided with a body fat measurement function according to the second aspect is characterized in that the control processing section displays, at the time of measurement of body fat of the person, check items to be used for determining whether or not the person has a pacemaker therein and performs processing for measuring body fat of the person only when the pacemaker check means determines that the person does not have a pacemaker and when the pacemaker is determined not to exist. Therefore, the person can ascertain safety before measuring body fat.

BRIEF DESCRIPTION OF THE DRAWINGS

FIGS. 5A to 5D are signal waveform diagrams showing operation of the TV,remote control unit performed at the time of measurement of body fat according to the embodiment of the invention;

DETAILED DESCRIPTION OF THE PREFFERED EMBODIMENTS

Figure 1B:
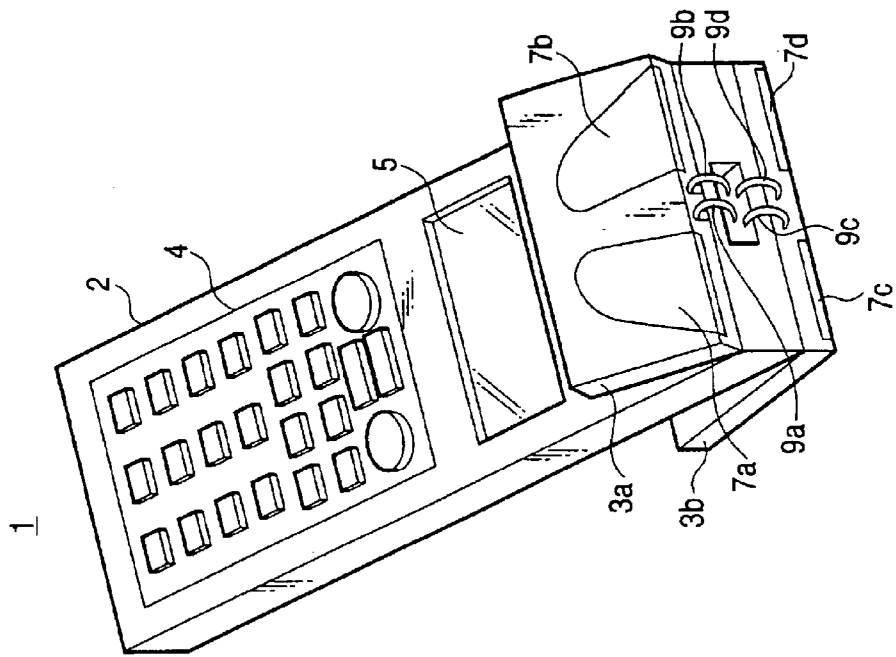
FIGS. 1A and 1B are perspective views showing configuration of a TV remote control unit provided with a body fat measuring function according to an embodiment of the invention.
Figure 1A:
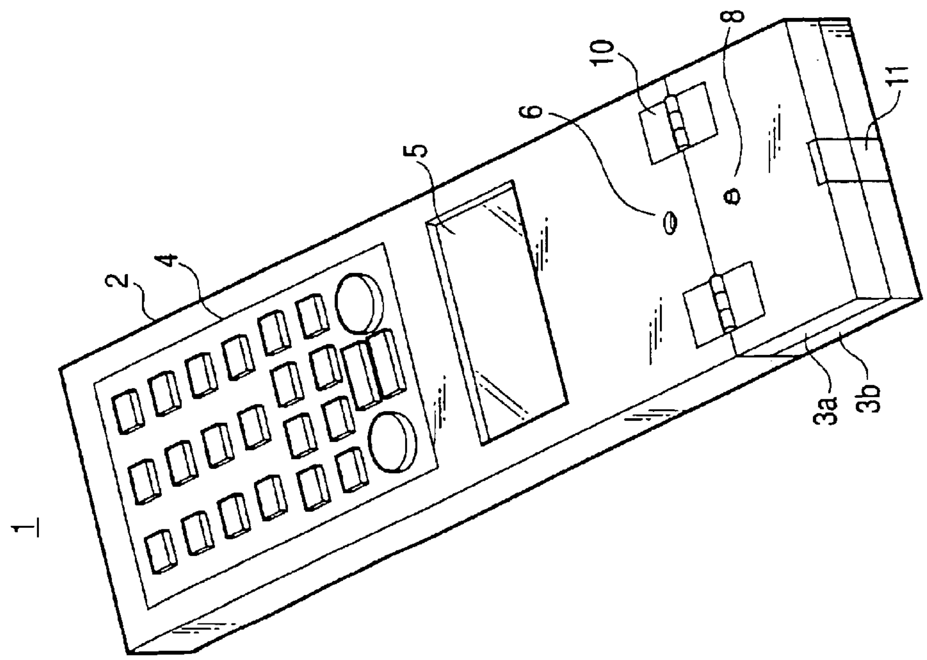

An embodiment of the invention will be described here in below with reference to the accompanying drawings. FIGS. 1A and 1B are perspective views showing the structure of a TV remote control unit provided with a body fat measurement function according to an embodiment of the invention. FIG. 1A is a perspective view showing the structure of the TV remote control unit when used for normally operating a TV set. FIG. 1B is a perspective view showing the structure of the TV remote control unit when used for measuring body fat.

A TV remote control unit 1 enables selection of a TV broadcast channel or a recording channel on a video recorder, measurement of body fat of a user, and display of the result of measurement of body fat on a TV screen. The TV remote control unit is constituted of a main body section 2 and open/close sections 3*a*, 3*b*.

The main body section 2 is provided with a key operation section 4, a liquid-crystal display section 5, and a measurement switch 6. A projection 8 is provided on the front of the open/close section 3*a*, and a pair of current application electrodes 7*a*, 7*b* to be used for measuring bio-impedance are provided at the inside of the open/close section 3*a*. Further, another pair of voltage measurement electrodes 7*c*, 7*d* to be used for measuring bio-impedance are provided at the inside of the open/close section 3*b*. The current application electrode 7*a* and the voltage measurement electrode 7*c* are connected together by means of an unillustrated electric cable provided in the main body section 2. The current application electrode 7*b* and the voltage measurement electrode 7*d* are connected together by means of an unillustrated electric cable provided in the main body section 2. The current application electrode 7*a* is connected to a circuit provided within the main body section 2 via an electric cable 9*a*. The current application electrode 7*b* is connected to a circuit provided in the main body section 2 via an electric cable 9*b*. The voltage measurement electrode 7*c* is connected to a circuit provided in the main body section 2 via an electric cable 9*c*. The voltage measurement electrode 7*d* is connected to a circuit provided in the main body section 2 via an electric cable 9*d*.

The open/close sections 3*a*, 3*b* are provided at positions close to the user when the remote control unit 1 is in use and secured on the main body section 2 in a reclosable manner with hinges 10. Force is exerted on the open/close sections 3*a*, 3*b* so as to open the same vertically at all times by means of unillustrated spring members. The open/close sections 3*a*, 3*b* are held in a closed state by engagement of a latch section 11 (FIG. 1A). By releasing the latch section 11 from the engaged state, the open/close sections 3*a*, 3*b* are opened by the force of the spring members and remain in a half-open state (FIG. 1B).

When the open/close section 3*a* is brought into a fully-opened state from the half-open state, the measurement switch 6 provided on the main body section 2 is pressed by the projection 8 provided on the open/close section 3*a*. When the open/close sections 3*a*, 3*b* are opened, the current application electrodes 7*a*, 7*b* and the voltage measurement electrodes 7*c*, 7*d* are positioned at the locations close to the user when the TV remote control unit 1 is in use.

When body fat is not measured, the TV remote control unit 1 is used while the current application electrodes 7*a*, 7*b* and the voltage measurement electrodes 7*c*, 7*d* are stored by closing the open/close sections 3*a*, 3*b*. When body fat is measured, the latch section 11 is released from the engaged state, thereby opening the open/close sections 3*a*, 3*b*. The current application electrodes 7*a*, 7*b* and the voltage measurement electrodes 7*c*, 7*d* are eventually exposed, thereby enabling measurement of bio-impedance. Bio-impedance is measured by the user pinching the current application electrode 7*a* and the voltage measurement electrode 7*c* with, e.g., the left thumb and forefinger and pinching the current application electrode 7*b* and the voltage measurement electrode 7*d* with, e.g., the right thumb and forefinger, while the open/close sections 3*a*, 3*b* are pressed and held in a fully-opened state. At this time, the measurement switch 6 provided on the main body section 2 is pressed by the projection 8 provided on the open/close section 3*a*, thereby starting supply of an electric current to the current application electrodes 7*a*, 7*b*. As a result, bio-impedance is measured.

Figure 2:
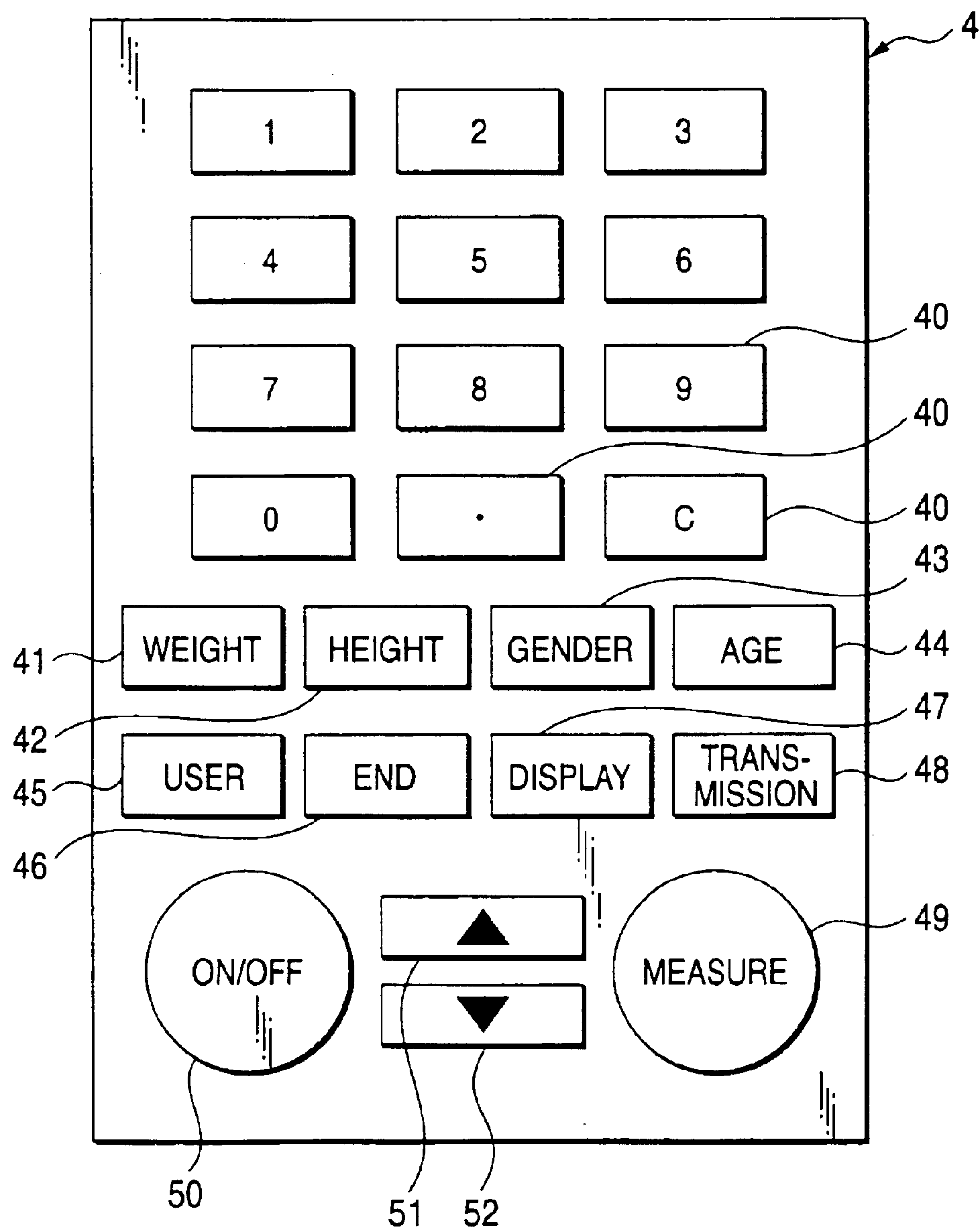
FIG. 2 is a block diagram showing a key operation section of the TV remote control unit shown in FIG. 1.

FIG. 2 is a block diagram showing the key operation section 4 provided on the TV remote control unit 1 shown in FIG. 1. The key operation section 4 comprises a plurality of ten-key numeric pads 40; a weight input key 41; a height input key 42; a gender input key 43; an age input key 44; a user select key 45; an end key 46; a display changeover 47; a transmission key 48; and a measurement key (body fat measurement key) 49. The key operation section 4 has a power key 50 to be used for activating or deactivating power of a TV set, and volume keys 51, 52 for controlling a volume level of sound output from the TV set.

The measurement key 49 is to be operated when a TV function mode is switched to a body fat measurement mode. The end key 46 is operated to terminate the body fat measurement mode and switch the body fat measurement mode to the TV function mode. The ten-key numeric pads 40 are operated to select a TV broadcast channel and set body data to be used for measuring body fat, such as weight, height, gender, and age. The body data are set in the body fat measurement mode by pressing each of the weight input key 41, the height input key 42, the gender key 43, and the age input key 44, and then entering a numerical value through actuation of the ten-keypads 40. The user select key 45 is operated to select a user (i.e., a person to be subjected to measurement) who is to be subjected to measurement of body fat. The display changeover key 47 is operated to switch the display type of a measurement result to be displayed on the TV set. The transmission key 48 is operated to transmit the body data and the bio-impedance to the TV set.

Figure 3:
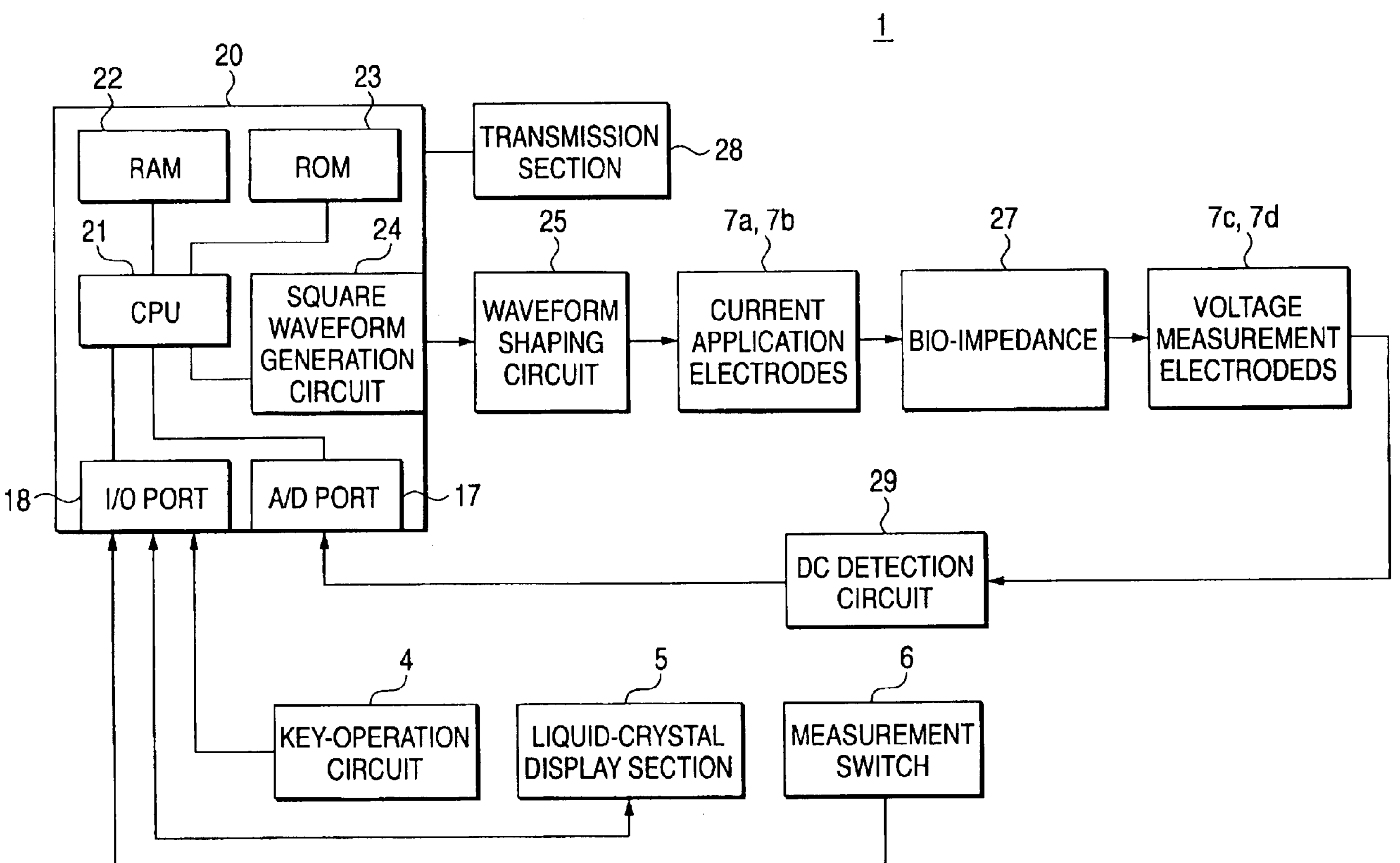
FIG. 3 is a block diagram showing an electrical configuration of a TV remote control unit provided with a body fat measurement function according to an embodiment of the invention.

FIG. 3 is a block diagram showing the electrical configuration of the TV remote control provided with the body fat measurement function according to one embodiment of the invention. In the TV remote control unit 1, a microcomputer 20 basically comprises ROM 23 in which is stored information, such as programs required to control the TV remote control unit 1; RAM 22 for storing information required to process data; a CPU 21 which performs control and processing operations on the basis of the information output from the ROM 23 and the RAM 22; and an I/O port 18 which inputs external information to the CPU 21 or outputs information to the outside. The microcomputer 20 further comprises a square wave generation circuit 24 for producing a square wave signal of predetermined frequency (e.g., 50 KHz), and an analog-to-digital port 17 serving as an analog-to-digital converter circuit for converting an analog voltage input from a DC detection circuit 29 to be described later into a digital value.

The I/O port 18 of the microcomputer 20 is connected to the key operation section 4 having a plurality of keys to be used for setting a channel or mode of the TV set; to the liquid-crystal display section 5 for displaying setting information and operation information; and to the measurement switch 6 to be turned on at the time of measurement of body fat. The microcomputer 20 is further connected to a transmission section 28 which transmits, to the TV set, an operation signal corresponding to the nature of key operation performed by way of the key operation section 4, in the form of an infrared-ray signal.

The TV remote control unit 1 comprises a waveform shaping circuit 25 which shapes a square signal output from the square waveform generation circuit 24 into a sinusoidal waveform signal; the pair of current application electrodes 7*a*, 7*b*, which constitute a closed circuit upon contact with the body of the user and cause an electric current originating from the sinusoidal waveform signal output from the waveform shaping circuit to flow through the user's body; the pair of voltage measurement electrodes 7*c*, 7*d*, which extract a potential difference between the current application electrodes 7*a*, 7*b*, the difference originating from the current flowing through the user's body, as a measurement voltage pertaining to bio-impedance 27 of the user; and the DC detection circuit (d.c. detection circuit) 29 for subjecting the voltage extracted by the voltage measurement electrodes 7*c*, 7*d* to d.c. detection.

Particularly, in the embodiment, the current application electrode 7*a* and the voltage measurement electrode 7*c* are connected together, and the current application electrode 7*b* and the voltage measurement electrode 7*d* are connected together. Thus, there is adopted an electrode configuration of essentially two-electrode type.

In the remote control unit 1 shown in FIG. 1, the square waveform generation circuit 24 is provided in the microcomputer 20. However, the square waveform generation circuit 24 is not limited to the inside of the microcomputer 20 but may be provided outside the microcomputer 20.

Further, the waveform shaping circuit 25 is provided at the outside of the microcomputer 20. However, the waveform shaping circuit 25 is not limited to the outside of the microcomputer 20 but may be provided in the microcomputer 20.

Figure 4:
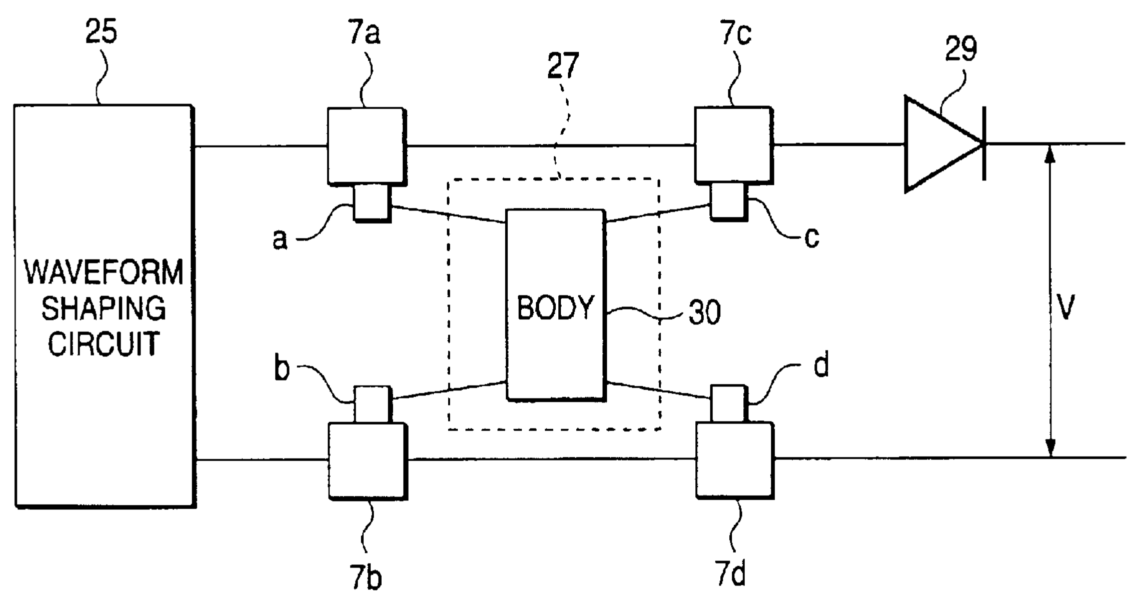
FIG. 4 is a block diagram showing a detailed configuration of the TV remote of two-electrode type according to the embodiment of the invention.

FIG. 4 is a block diagram showing the detailed configuration of the above-described two-electrode type. In FIG. 4, reference numeral 30 designates the user's body; "a" denotes the user's left thumb; "c" denotes the user's left forefinger; "b" denotes the user's right thumb; and "d" denotes the user's left forefinger.

At the time of measurement of body fat, the user's left thumb "a," for example, is brought into contact with the current application electrode 7*a*, and the user's left forefinger "c" is brought into contact with the voltage application electrode 7*c*. Further, the user's right thumb "b" is brought into contact with the voltage application electrode 7*b*, and the right forefinger "d" is brought into contact with the voltage application electrode 7*d*. The sinusoidal waveform signal applied between the current application electrodes 7*a* and 7*b* flows through, in this sequence, the user's left thumb "a," the left forefinger "c," the body 30, the user's right thumb "b," and the right forefinger "d." Specifically, the electric current stemming from the sinusoidal waveform signal flows through the bio-impedance 27, and a voltage developing across the bio-impedance 27 is extracted by the voltage application electrodes. 7*c*, 7*d*. The voltage is further subjected to d.c. detection performed by the DC detection circuit 29. The voltage V that has been subjected to d.c. detection is a measurement voltage pertaining to the bio-impedance 27.

FIGS. 5A to 5D are signal waveform diagrams showing operation of the TV remote control unit 1 of the embodiment performed at the time of measurement of body fat. FIG. 5A shows a square signal output from the square waveform generation circuit 24 of the microcomputer 20; FIG. 5B shows a sinusoidal waveform signal formed by shaping the square signal with the waveform shaping circuit 25; FIG. 5C shows a voltage.(measurement voltage) output from the DC detection circuit 29 when the user has high body fat content and has the large bio-impedance 27; and FIG. 5D shows a voltage (measurement voltage) output from the DC detection circuit 29 when the user is low body fat content and has the low bio-impedance 27.

Figure 6:
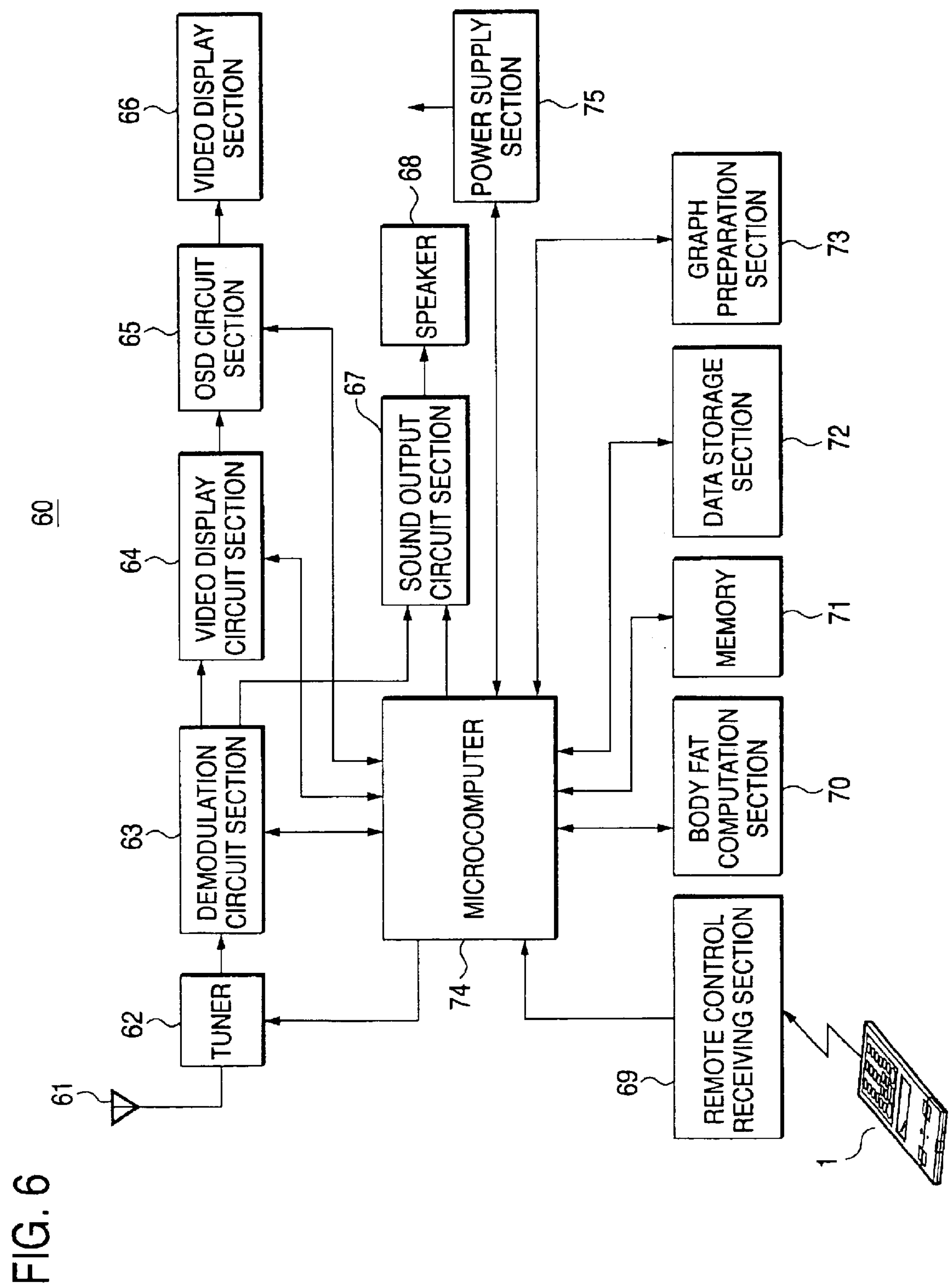
FIG. 6 is a block diagram showing electrical configuration of a TV set to be operated by the TV remote control unit of the invention.

FIG. 6 is a block diagram showing the electrical configuration of the TV set operated by the remote control unit 1 of the embodiment. In FIG. 6, a TV set 60 comprises an antenna 61 for receiving a TV radio wave; a tuner 62; a demodulation circuit section 63; a video display circuit section 64; an OSD circuit section 65; a video display section 66; a sound output circuit section 67; a speaker 68; a remote control receiving section 69; a body fat computation section 70; memory 71; a data storage section 72; a graph preparation section 73; a microcomputer 74; and a power supply section 75 for supplying power to the individual sections.

The TV set 60 receives a TV broadcast signal in the form of a high-frequency signal via the antenna 61 by putting the frequency received by the tuner 62 in tune with the frequency of the selected channel under control of the microcomputer 74. The thus-received high-frequency signal is demodulated by the demodulation circuit section 63, and the video display circuit section 64 reproduces a video signal. Further, the sound output circuit section 67 reproduces a sound signal. The video signal reproduced by the video display circuit section 64 is sent to the video display section 66 via the OSD circuit section 65, thereby displaying a video of the TV broadcast on the video display section 66. The OSD circuit section 65 is a circuit for displaying, in the form of an OSD display, a TV broadcast channel and a result of measurement of body fat on the video appearing on the video display section 66. The sound signal reproduced by the sound output circuit section 67 is sent to the speaker 68, and the sound of the TV broadcast is output from the speaker 68.

The remote control receiving section 69 receives an infrared-ray signal transmitted from the TV remote control unit 1. The body fat computation section 70 computes percent body fat from body data, which are included in the body fat measurement signal received by the remote control receiving section 69 and represent weight, height, gender, and age, and bio-impedance. The memory 71 stores an animation character image corresponding to the percent body fat computed by the body fat computation section 70. The data storage section 72 stores the percent body fat computed by the body fat computation section 70 and the body data used at the time of computation of the percent body fat. The graph preparation section 73 shows a transition :in percent body fat in the form of a graph, such as a kinked line and a bar graph, on the basis of the body data stored in the data storage section 72.

When an unillustrated power switch provided on the TV set 60 has been operated or when the remote control receiving section 69 has received an ON/OFF signal from the TV remote control unit 1, the microcomputer 74 controls activation/deactivation of the power supply section 75. When the remote control receiving section 69 has received a channel section signal, the microcomputer 74 causes the tuner 62 to bring the received frequency in tune with the frequency of the selected channel, thereby displaying a video of the TV broadcast of the selected channel on the video display section 66, and the sound of the TV broadcast is output from the speaker 68.

When the remote control receiving section 69 has received the body fat measurement signal, the microcomputer 74 causes the body fat computation section 70 to compute percent body fat. The thus-computed percent body fat is displayed on a video of the TV broadcast appearing on the video display section 66 in the form of an OSD display. When the remote control receiving section 69 has received a display changeover signal after the microcomputer 74 has displayed the percent body fat on the video display section 66, an animation character corresponding to the percent body fat is read from the memory 71, and the thus-read character is displayed on the video display section 66 in the form of an OSD. Further, past data are read from the data storage section 72, and the graph preparation section 73 prepares a transition graph of percent body fat along with the data obtained this time. The graph is displayed on the video display section 66 in the form of an OSD display. When an end signal has been received, display of a result of measurement of body fat is completed, thereby ordinarily displaying the TV broadcast.

Figure 7:
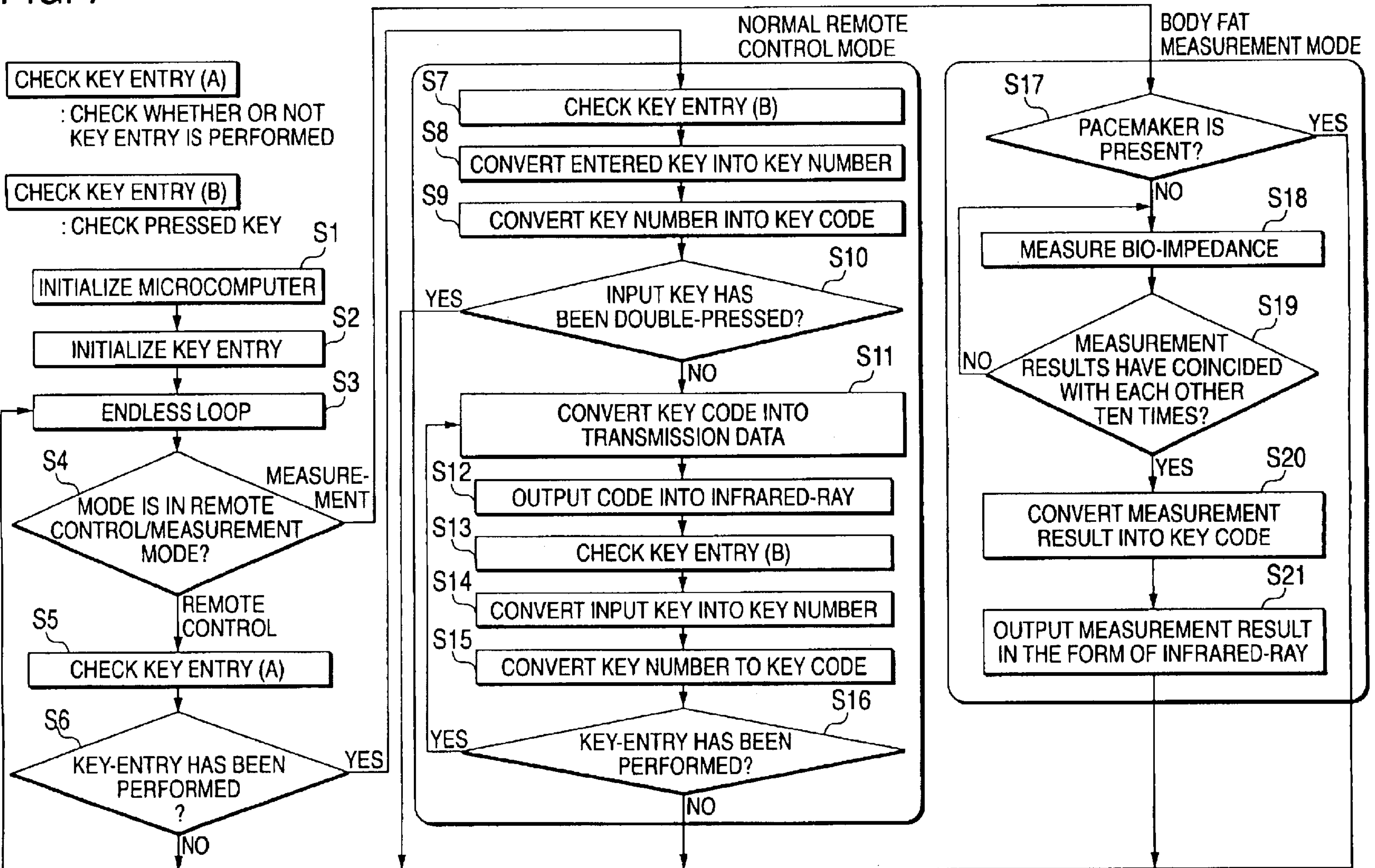
FIG. 7 is a flowchart showing operation of the TV remote control unit according to the embodiment.

FIG. 7 is a flowchart showing operation of the TV remote control unit 1 of the embodiment. Operation of the TV remote control unit 1 of the embodiment will now be described hereinbelow by reference to the flowchart and FIGS. 1 through 6.

After the microcomputer 20 has been set to the initial settings in step S1, key entry of the TV remote control unit 1 is set to initial settings in step S2.

In step S4, a determination is made as to as to whether the current mode is a mode of using the TV remote control unit 1 as an ordinary TV remote control unit or of used for measuring body fat. When the current mode is determined as a mode for using the TV remote control unit 1 so as to measure body fat, processing proceeds to step S17. The liquid-crystal section 5 displays check items to be used for checking whether or not the user has a pacemaker (pacemaker check means) . The user completes such checking. If the result of check reveals that the user has a pacemaker, processing required for effecting measurement is stopped for reasons of the risk of adverse influence being inflicted on the pacemaker during measurement. If the result of checking reveals that the user does not have any pacemaker, measurement may be performed, and processing proceeds to step S18.

In step S18, the body data pertaining to a person which desires measurement of body fat, such as weight, height, and age, are input to the RAM 22 by actuation of the keys of the TV remote control unit 1 (body data setting means). In step S18, a square wave signal of, e.g., 50 KHz, output from the square wave generation circuit 24 of the microcomputer 20 is converted into a sinusoidal waveform signal through shaping performed by the waveform shaping circuit 25. While the sinusoidal signal is applied to the current application electrodes 7*a*, 7*b*, the user pinches the current application electrode 7*a* and the voltage measurement electrode 7*c* with the left thumb "a" and the left forefinger "c" and the current application electrode 7*b* and the voltage measurement electrode 7*d* with the right thumb "b" and the right forefinger "d."

As a result, a feeble current flows into the body 30 of the user, and a voltage difference corresponding to the degree of fat is caused to develop between the voltage measurement electrodes 7*c* and 7*d* by the bio-impedance 27. A voltage attributable to the voltage difference is output from a node between the voltage measurement electrodes 7*c*, 7*d*. The voltage output from the node between the voltage measurement electrodes 7*c*, 7*d* is delivered to the CD detection circuit 6. The voltage is input to the analog-to-digital port 17 of the microcomputer 20 as a DC detection voltage. In step S18, the sinusoidal signal is caused to flow into the body 30 of the user, thereby measuring the bio-impedance 27 of the user. The DC detection voltage corresponding to the bio-impedance 27 is input to the A/D port 17 of the microcomputer 20 as the measurement result.

In step S19 (measurement means), the microcomputer 20 converts the result of measurement obtained through processing pertaining to step S18 into a digital value through the A/D port 17. A determination is made as to whether or not a match arises between the digital values a predetermined, consecutive number of times; for example, ten times, within a predetermined sampling cycle. If a match is determined to have consecutively arisen ten times, the digital value (i.e., the measurement result) is deemed as being a highly reliable value, and processing proceeds to step S20.

In step S20, the measurement result is converted into a key code. In step. S21, the measurement result that has been converted into a key code is output from the transmission section 28 of the TV remote control unit 1 with an infrared-ray and transmitted to the TV set 60. As a result, the TV set 60 receives the measurement result and performs computation through use of the microcomputer 74 and the body fat computation section 70, both being provided in the TV set 60. Information as to whether or not the user has high body fat content is displayed on the screen. After processing pertaining to step S21 has been completed, processing returns to step S3.

When the measurement result output from the TV remote control unit 1 has been received by the TV set 60, body fat is displayed in numerical values on the TV screen. When the display changeover key 47 of the remote control unit 1 is pressed, the numerical value of body fat is switched to an animation character display. When the display changeover key 47 is pressed further, the display is switched to the display of a graph, such as a kinked graph or a bar graph.

In step S4, when the mode is determined to have been set to the mode of a normal TV remote control, processing proceeds to step S5. Key entry operation of the TV remote control unit 1 is checked (i.e., only occurrence of key entry is checked) If in step S6 key entry is determined to have arisen, processing proceeds to step S7. In contrast, key entry is determined to have arisen, and processing returns to step S3.

In step S7, a check is made as to which one, if any, of the keys of the TV remote control unit 1 is pressed. The input key pressed this time is converted into a key number in step S8. In step S9, the key number is converted into a key code. In step S10, if occurrence of double-pressing of the input key is determined not to have arisen, processing proceeds to step S11. In contrast, if double pressing of the key input is determined to have arisen, processing returns to step S3.

In step S11, the key code is converted into transmission data. In step S12, the key code converted into the transmission data is output from: the TV remote control unit 1 in the form of an infrared-ray. In step S13, the microcomputer 74 of the TV set 60 checks a key of the remote control unit 1 by way of which the key entry has been performed. In step S14, the entry key is converted into a key number. Further, in step S15, the key number is converted into a key code. In step S16, a determination is made as to whether or not key entry is performed, by mean s of the key code. If key entry is determined to be performed, processing returns to step S11. Processing pertaining to steps S11 to S15 is repeated. In contrast, in step S16 the key entry is determined not to be performed, processing returns to step S3.

In the embodiment, when body fat of the user is measured, check items are first displayed for checking whether or not the user has a pacemaker embedded in the body. The user ascertains that he/she does not have any pacemaker. If the results shows that the user does not have a pacemaker, body fat is measured. Thus, high safety is ensured.

The body of the user is brought into contact with the current application electrode and the voltage application electrode. A digital value obtained when a match is determined to have arisen, a predetermined number of times, between digital values corresponding to electrode voltages within a predetermined sampling cycle is taken as a result of measurement of bio-impedance. Hence, a highly stable measurement result of bio-impedance can be obtained.

In the embodiment, for example, the user pinches the current application electrode 7*a* and the voltage measurement electrode 7*c* with the left thumb "a" and the left forefinger "c" and the current application electrode 7*b* and the voltage measurement electrode 7*d* with the right thumb "b" and the right forefinger "d." The user can measure body fat even when pressing the current application electrode 7*a* with the left thumb "a" and the current application electrode 7*b* with the right thumb "b." In short, the user can measure body fat, so long as, e.g., the left hand of the user comes into contact with either the current application electrode 7*a* or the voltage measurement electrode 7*c* and the right hand comes into contact with the current application electrode 7*b* or the voltage measurement electrode 7*d*.

As has been described, according to the first aspect of the invention, setting of body data to be used for measuring body, such as weight, height, and gender, and measurement of bio-impedance are performed by a TV remote control unit. A TV set computes body fat from the body data and bio-impedance. A result of computation of body fat is displayed. Hence, there is no necessity for additionally purchasing a body fat measurement device, which is available as a single commodity product, thereby lessening economical burden imposed on a user.

The TV remote control unit is always available within arm's reach in a home where a TV set is disposed. The user can feel free to measure body fat whenever he/she desires. Since a result of measurement of body fat is displayed on a TV screen, a display of the result of measurement of body fat is large and easy to view. The result of measurement of body fat can be displayed in various manners, thereby providing the user with a pleasure to see a result.

Setting of physique data to be used for measuring body fat, such as weight, height, age, and gender, and measurement of bio-impedance are performed by way of the TV remote control unit. The TV set having high processing capability computes body fat from the physique data and the bio-impedance, and a result of computation of body fat is displayed. Thus, a body fat measurement function can be added to the TV remote control unit without deteriorating the original performance of the unit and without a cost hike.

An essentially two-electrode type is adopted for electrodes to be used for measuring bio-impedance of a user. Hence, a construction for measuring bio-impedance becomes simple.

At the time of measurement of body fat of the user, check items are first output, to enable the user to check whether or not a pacemaker is embedded in the body. After the user has set such that no pacemaker is provided in the body and the user has been determined not to have a pacemaker, body fat can be measured, thereby improving safety.

After the safety has been ascertained, body data which are required to measure body fat of the user and include weight, age, height, and gender, all pertaining to the user, are set in the microcomputer through key-operation of the key operation section. Subsequently, the body of the user is brought into contact with the current application electrode. In the case where a digital value is obtained when a match arises between digital values a predetermined number of times, the digital value is taken as a result of measurement of bio-impedance to be used for computing the body fat of the user. In this way, the digital value obtained when a match has arisen between the digital values a predetermined number of times is taken as a result of measurement of the bio-impedance. Hence, a highly reliable measurement result is obtained.

According to the second aspect of the invention, setting of body data to be used for measuring body fat, such as weight, height, age, and gender, and measurement of bio-impedance are performed by way of the TV remote control unit. The TV set computes body fat from the body data and the bio-impedance and displays a result of computation of body fat. Hence, there is no necessity for additionally purchasing a body fat measurement device, which is available as a single commodity product, thereby lessening economical burden imposed on a user. The TV remote control unit is always available within arm's reach in a home where a TV set is disposed. The user can feel free to measure body fat whenever he/she desires. Since a result of measurement of body fat is displayed on a TV screen, a display of the result of measurement of body fat is large and easy to view. The result of measurement of body fat can be displayed in various manners, thereby providing the user with a pleasure to see a result.

Setting of physique data to be used for measuring body fat, such as weight, height, age, and gender, and measurement of bio-impedance are performed by way of the TV remote control unit. The TV set having high processing capability computes body fat from the physique data and the bio-impedance, and a result of computation of body fat is displayed. Thus, a body fat measurement function can be added to the TV remote control unit without deteriorating the original performance of the unit and without a cost hike.

An essentially two-electrode type is adopted for electrodes to be used for measuring bio-impedance of a user. Hence, a construction for measuring bio-impedance becomes simple.

The body of the user is brought into contact with the current application electrode and the voltage application electrode. A digital value obtained when a match is determined to have arisen, a predetermined number of times, between digital values corresponding to electrode voltages within a predetermined sampling cycle is taken as a result of measurement of bio-impedance. Hence, a highly stable measurement result of bio-impedance can be obtained.

An essentially two-electrode type is adopted for electrodes to be used for measuring bio-impedance of a user. Hence, a construction for measuring bio-impedance becomes simple.

According to the third aspect of the invention, the TV remote control unit with a body fat measurement function defined in the second aspect is characterized in that the electric signal generation means has a square waveform generation circuit for generating a square signal of predetermined frequency, and a waveform shaping circuit for converting the square signal output from the square waveform generation circuit into a sinusoidal waveform signal through waveform shaping. A highly accurate sinusoidal waveform signal can be used for measuring the bio-impedance of the user. Further, if the frequency of the square signal is changed, the frequency of the output sinusoidal waveform signal can also be changed. Hence, the accuracy of measurement of impedance is improved, so long as the frequency of the sinusoidal waveform signal has been set to a frequency at which the minimum error arises in an error of measurement of bio-impedance beforehand.

According to the fourth aspect of the invention, the TV remote control unit provided with a body fat measurement function defined in the second aspect is characterized in that the bio-impedance measurement electrode comprises a pair of current application electrodes which constitute a closed circuit when coming into contact with the body of a user and cause an electric signal output from the electric signal generation means to flow through the body of the user; and a pair of voltage measurement electrodes which take, as a measurement voltage relevant to bio-impedance of the user, a potential difference arising between the current application electrodes from the electric current flowing through the body of the user. One electrode of the pair of current application electrodes and one electrode of the pair of voltage measurement electrodes are connected together. Further, the remaining electrode of the pair of current application electrodes and the remaining electrode of the pair of voltage measurement electrodes are connected together, thereby realizing an essentially two-electrode type. Hence, measurement of bio-:impedance substantially requires four electrodes, but the number of electrodes is reduced to substantially two electrodes. The configuration of the TV remote control unit is simplified by the amount corresponding to the number of electrodes reduced.

According to the fifth aspect of the invention, the TV remote control unit provided with a body bat measurement function defined in the second aspect is characterized in that the voltage extracted from the bio-impedance measurement electrode is subjected to d.c. detection performed by the d.c. detection circuit. Further, the detection voltage obtained through d.c. detection is converted into a digital value by means of an analog/digital circuit. The digital value obtained when a match has arisen between the digital values a predetermined number of times is taken as a result of measurement of bio-impedance to be used for computing percent body fat. Hence, a highly stable result of measurement of bio-impedance is obtained.

According to the sixth aspect of the invention, the TV remote control unit provided with a body fat measurement function defined in the second aspect is characterized in that, at the time of measurement of body fat of the user, check items to be used for determining whether or not the user has a pacemaker are output. Only when the user has effected settings such that he/she does not have any pacemaker and when the user is determined not to have any pacemaker, processing for measuring body fat of the user is carried out. Hence, the user can ascertain safety before measuring body fat.

What is claimed is:

1. A TV remote control unit comprising:

a key operation section having a plurality of keys to be used for performing operations for setting a channel of a TV set and a mode;

a transmission section for transmitting, to the TV set, an operation signal corresponding to key operation performed by way of the key operation section;

a microcomputer which controls the key operation section and the transmission section and performs predetermined processing;

a square waveform generation circuit for generating a square signal of predetermined frequency, a waveform shaping circuit for converting the square signal output from the square waveform generation circuit into a sinusoidal waveform signal;

a pair of current application electrodes which constitute a closed circuit upon contact with the body of a person whose body fat is to be measured and causes an electric current stemming from a sinusoidal waveform signal output from the waveform shaping circuit to flow through the body of the person;

a pair of voltage measurement electrodes for extracting a potential difference between the current application electrodes developing from the current flowing through the body of the person as a measurement voltage relevant to bio-impedance of the person;

a d.c. detection circuit for subjecting the voltage extracted from the voltage measurement electrodes to d:c. detection; and an analog/digital conversion circuit for converting into a digital value a detection voltage having been subjected to d.c. detection by the d.c. detection circuit, wherein a substantial two-electrode type is established by connecting one of the pair of current application electrodes to one of the pair of voltage measurement electrodes and connecting the other electrode of the pair of current application electrodes to the other electrode of the pair of voltage measurement electrodes, wherein the microcomputer comprises:

pacemaker checking means that displays check items to be used for determining whether or not the person has a pacemaker at the time of measurement of body fat of the person;

body data setting means which sets body data required for measuring body fat of the person, including the person's weight, age, height, and gender, when the pacemaker check means determined that the person does not have a pacemaker and when the pacemaker is determined not to exist; and measurement means which, when the body of the person has been brought into contact with at least either the current application electrodes or the voltage measurement electrodes, takes a digital value obtained when a match has consecutively arisen between digital values a predetermined number of times within a predetermined sampling cycle as a result of measurement of bio-impedance required for computing body fat of the person, and wherein the result of measurement of the bio-impedance and the body data are transmitted to the TV set by way of the transmission section; body fat of the person is computed on the basis of the bio-impedance and body data received by the TV set; and the result of computation is displayed on a screen of the TV set.

2. A TV remote control unit comprising:

a key operation section having a plurality of keys to be used for performing operations for setting a channel of a TV set and a mode;

a transmission section for transmitting, to the TV set, an operation signal corresponding to key operation performed by way of the key operation section;

a control processing section which controls the key operation section and the transmission section and performs predetermined processing;

electric signal generation means for generating an electric signal of predetermined frequency; and a bio-impedance measurement electrode which constitutes a closed circuit upon contact with the body of a person whose body fat is to be measured, causes an electric signal output from the electric signal generation means to flow through the body of the person, and extracts a potential difference developing in the body of the person from the current flowing through the body of the person as a measurement voltage pertaining to bio-impedance of the person, wherein the control processing section comprises:

body data setting means which sets body data required for measuring body fat of the person, including the person's weight, age, height, and gender; and measurement means which, when the body of the person has been brought into contact with at least either a pair of current application electrodes or a pair of voltage measurement electrodes, takes a digital value obtained when a match has arisen between digital values a predetermined number of times within a predetermined sampling cycle as a result of measurement of bio-impedance required for computing body fat of the person, and wherein the result of measurement of the bio-impedance and the body data are transmitted to the TV set by way of the transmission section, and the TV set computes body fat of the person from the receive bio-impedance and body data and displays the result of computation on a screen of the TV set.

3. The TV remote control unit according to claim 2, wherein the electric signal generation means has a square waveform generation circuit from generating a square waveform signal of predetermined frequency and a waveform shaping circuit for converting a square signal output from the square waveform generation circuit into a sinusoidal waveform signal, and outputs a sinusoidal waveform signal.

4. The TV remote control unit according to claim 2, wherein the bio-impedance measurement electrode has a pair of current application electrodes which constitute a closed circuit upon contact with the body of a person to be measured and causes an electric current stemming from a sinusoidal waveform signal output from the waveform shaping circuit to flow through the body of the person and a pair of voltage measurement electrodes for extracting a potential difference between the current application electrodes developing from the current flowing through the body of the person as a measurement voltage relevant to bio-impedance of the person, and the bio-impedance measurement electrode establishes a substantial two-electrode type by connecting one of the pair of current application electrodes to one of the pair of voltage measurement electrodes and connecting the other electrode of the pair of current application electrodes to the other electrode of the pair of voltage measurement electrodes.

5. The TV remote control unit according to claim 2, wherein a d.c. detection circuit subjects the voltage extracted from the voltage measurement electrodes to d.c. detection, an analog/digital conversion circuit converts into a digital value a detection voltage having been subjected to d.c. detection by the d.c. detection circuit, and a digital value obtained when a match has consecutively arisen between digital values a predetermined number of times within a predetermined sampling cycle is taken as a result of measurement of bio-impedance required for computing body fat of the person.

6. The TV remote control unit according to claim 2, wherein the control processing section displays, at the time of measurement of body fat of the person, check items to be used for determining whether or not the person has a pacemaker and performs processing for measuring body fat of the person only when the pacemaker check means determines that the person does not have a pacemaker and when the pacemaker is determined not to exist.

* * * * *